(12) United States Patent
Hermann et al.

(10) Patent No.: US 8,510,127 B2
(45) Date of Patent: Aug. 13, 2013

(54) METHOD AND SYSTEM FOR DEVELOPING AND DELIVERING A THERAPEUTIC MEAL PLAN PROGRAM

(75) Inventors: James William Hermann, Franklin, WI (US); Vivian Marie Roe, St. Francis, WI (US)

(73) Assignee: TherapEase Cuisine, Inc., Greenfield, WI (US)

( * ) Notice: Subject to any disclaimer, the term of this patent is extended or adjusted under 35 U.S.C. 154(b) by 51 days.

(21) Appl. No.: 12/133,025

(22) Filed: Jun. 4, 2008

(65) Prior Publication Data

US 2009/0307007 A1 Dec. 10, 2009

(51) Int. Cl.
*G06Q 10/00* (2006.01)
*G06Q 50/00* (2006.01)

(52) U.S. Cl.
USPC .................................. 705/2; 705/3; 600/300

(58) Field of Classification Search
USPC ........................................ 705/2, 3; 600/300
See application file for complete search history.

(56) References Cited

U.S. PATENT DOCUMENTS

| | | | |
|---|---|---|---|
| 5,514,656 A | 5/1996 | Cope et al. | |
| 5,994,295 A * | 11/1999 | Khoo et al. | 514/2 |
| 5,997,059 A | 12/1999 | Thomas | |
| 6,630,160 B1 | 10/2003 | Evans et al. | |
| 7,025,995 B2 | 4/2006 | Palpu et al. | |
| 7,303,770 B2 | 12/2007 | Fahey et al. | |
| 2004/0210456 A1* | 10/2004 | Kirchhoff et al. | 705/1 |
| 2006/0053184 A1* | 3/2006 | Grana | 707/204 |

OTHER PUBLICATIONS

"The Role of Dietary Supplements during Cancer Therapy1." Helen A Norman; Ritva R Butrum; Elain Feldman; David Heber; et al. The Journal of Nutrition; Nov. 2003; 133, 11S-I; Research Library p. 3794S.*

Recipe: foods to Eat Before and During chemotherapy??? Posted by *trudymom*; iVillage GardenWeb; http://ths.gardenweb.com/forums/load/specex/msg09184635229958.html.

The Clinical Guide to Oncology Nutrition; Oncology Nutrition Dietetic Practice Group; American Dietetic Association; http://www.eatright.org/cps/red/xchg/ada/hs.xsl/shop_7269_ENU_HTML.htm.

Amato, Paula MD et al.; "Estrogenic Activity of Herbs Commonly Used as Remedies for Menopausal Symptoms", Ovid website; https://ovidsp.tx.ovid.com/sp-3.4.2a/ovidweb.cgi; vol. 9(2), Mar. 2002, pp. 145-150.

Asamoto, Makoto, et al.; "Mammary Carcinomas Induced in Humans c-Ha-ras Proto-oncogene Transgenic Rats Are Estrogen-independent, but Responsive to D-Limonene Treatment", Japan J. Cancer Res., 93, 32-35, Jan. 2002.

Assinewe, V.A., et al.; "Extractable Polysaccharides of *Panax quinquefolius* L. (North American Ginseng) Root Stimulate TNFa production by Alveolar Macrophages", Phytomedicine, vol. 9, Issue 5, 2002, pp. 398-404.

(Continued)

*Primary Examiner* — Michelle Le
(74) *Attorney, Agent, or Firm* — Husch Blackwell LLP

(57) ABSTRACT

A system and method develops a customized meal plan for a patient based on a chemotherapy treatment regimen for the patient and delivers the corresponding food items of the meal plan to the patient. The customized meal plan is designed to mitigate the physical effects and nutritional losses associated with chemotherapy and other cancer related treatments, such as radiation therapy. As the medical condition of the patient changes, the meal plan can be revised to provide updated customization. The meal plan may be developed using information provided by the patient, a caregiver, such as a nurse or physician, or a combination thereof.

35 Claims, 3 Drawing Sheets

(56) References Cited

OTHER PUBLICATIONS

Attele, Anoja S., et al.; "Ginseng Pharmacology, Multiple Constituents and Multiple Actions", Beiochemical Pharmacology, vol. 58. pp. 1685-1693, 1999.

Belanger, James T.; "Perilly Alcohol: Applications in Oncology", Alternative Medicine Review, vol. 3, p. 448, No. 6, 1998.

Chen, Edith S., et al., "American Ginseng. III. Pharmacokinetics of Ginsenosides in the Rabbit", European Journal of Drug Metabolism and Pharmacokinetics, 1980, vol. 5, No. 3, p. 161-168.

Chlebowski, Rowan T., et. al.; "Dietary Fat Reduction and Breast Cancer Outcome: Interim Efficacy Results From the Women's Intervention Nutrition Study", Journal of the National Cancer Institute, vol. 98, No. 24, Dec. 20, 2006.

Crowell, Pamela L.; "Human Metabolism of the Experimental Cancer Therapeutic Agent-d-limonene", Cancer Chemother Pharmaco (1994) 35: 31-37.

Cui, Yong et al., et. al.; "Association of Ginseng Use with Survival and Quality of Life Among Breast Cancer Patients", American Journal of Epidemiology, 2006; vol. 163, No. 7:645-53.

Doll, R. and Peto, R.; "The Causes of Cancer: Quantitative Estimates of Avoidable Risks of Cancer in the United States Today", JNCI, Oxford University Press, vol. 66(6) p. 1191-308, Jun. 1981.

Fleshner, Neil et al.; "Dietary Fat and Prostate Cancer"; The Journal of Urology, vol. 171, S19-S24, Feb. 2004.

Hardcastle, Ian R.; "Inhibition of Protein Prenylation by Metabolites of Limonene", Biochemical Pharmacology, 1999; vol. 57, pp. 801-809.

Hudes, Gary R.; "Phase I Pharmacokinetic Trail of Perillyl Alchohol (NSC 641066) in Patients with Refractory Solid Malignancies", Clinical Cancer Research, vol. 6, 3071-3080, Aug. 2000.

Kaji, Itaru; "Inhibition by D-Limonene of Experimental Hepatocarcinogenesis in Sprague-Dawley Rats Does Not Involve P21ras Plasma Membrane Association", UICC, Int. J. Cancer: 93, 441-444 (2001).

Low-Baselli, Alexandria; "Failure to Demonstrate Chemoprevention by the Monoterpene Perillyl Alcohol During Early Rat Hepatocarcinogenesis: A Cautionary Note", Oxford University Press, Carcinogenesis vol. 21, No. 10, pp. 1869-1877, 2000.

Mattisson, I. et al.; "Intakes of Plant Foods, Fibre and Fat and Risk of Breast Cancer—A Prospective Study in the Malmo Diet and Cancer Cohort", British Journal of Cancer (2004) 90, 122-127.

Missmer, Stacey A.; "Meat and Dairy Food Consumption and Breast Cancer: A Pooled Analysis of Cohort Studies", International Journal of Epidemiology, 2002; 31: 78-85.

Mokdad, Ali H.; "Actual Causes of Death in the United States, 2000", JAMA, Mar. 10, 2004—vol. 291, No. 10 p. 1238.

Pierce, John P. et al.; "Influence of a Diet Very High in Vegetables, Fruit, and fiber and Low in Fat on Prognosis Following Treatment for Breast Cancer", The Women's Healthy Eating and Living (WHEL) randomized trial. JAMA, Jul. 18, 2007; 298(3):289-98.

Predy, Gerald N. et al.; "Efficacy of an Extract of North American Ginseng Containing poly-furanosyl-pyranosyl-saccharides for Preventing Upper Respiratory Tract Infections: A Randomized Controlled Trial", CMAJ 2005: 173(9):1043-8.

Reddy, Bandaru S.; "Chemoprevention of Colon Carcinogenesis by Dietary Perillyl Alcohol", Cancer Research 57, 420-425, Feb. 1, 1997.

Ripple, Gregory H.; "Phase I Clinical and Pharmacokinetic Study of Perillyl Alcohol Administered Four Times a Day", Clinical Cancer Research, vol. 6, 390-396, Feb. 2000.

Shin, Hai Rim, et al.; "The Cancer-Preventive Potential of Panax Ginseng: A Review of Human and Experimental Evidence", Cancer Causes and Control 2000;11:565-576.

Steinmetz, Kristi A. and Potter, John D.; "Vegetables, Fruit, and Cancer. I. Epidemiology", Cancer Causes and Control. vol. 2, 1991.

Topham, E. J. and Wakelin, S. H.; D-Limonene Contact Dermatitis From Hand Cleaners, Contact Dermatis. Aug. 2003;49(2):108-9.

Uedo, Noriya et al., "Inhibition by D-limonene of Gastric Carcinogenesis Induced by N-methyl-N'-nitro-N-nitrosoguanidine in Wistar Rats", Article, Accepted Oct. 29, 1998. Available Online Apr. 21, 1999.

Vigushin, David M. et al.; "Phase I and Pharmacokinetic Study of D-limonene in patients with Advanced Cancer", Cancer Chemother Pharmacol (1998) 42: 111-117.

Vuksan, Vladimir, PhD, et al.; "American Ginseng (*Panax quinquefolius* L) Reduces Postprandial Glycemia in Nondiabetic Subjects and Subjects With Type 2 Diabetes Mellitus", Abstract, Arch Intern Med. 2000; 160:1009-1013.

Vuksan, Vladimir, PhD, et al.; :American Ginseng (*Panax quinquefolius* L.) Attenuates Postprandial Glycemia in a Time-Dependent but not Dose-Dependent Manner in Healthy Individuals, Abstract, The American Journal of Clinical Nutrition, 2001: 73-753-8.

Vuksan, Vladmir, PhD, et al.; "American Ginseng Imporves Glycemia in Individuals with Normal Glucose Tolerance: Effect of Dose and Time Escalation", Journal of the American College of Nutrition, vol. 19, No. 6, 738-744 (2000).

Yuan, Chun-Su, et al.; "Brief Communication: American Ginseng Reduces Warfarin's Effect in Healthy Patients, a Randomized, Controlled Trial", Abstract, Annals of Internal Medicine, Jul. 6, 2004, vol. 141 No. 1, 23-27; www.annals.org.

"TherapEase Cuisine™, Medco's Cancer Nutrition Program, Expands Capabilities to Food Shipments Directly to Patients' Homes", Jan. 23, 2012 /PRNewswire/—Medco Health Solutions, Inc.

\* cited by examiner

METHOD AND SYSTEM FOR DEVELOPING AND DELIVERING A THERAPEUTIC MEAL PLAN PROGRAM

BACKGROUND OF THE INVENTION

The present invention relates generally to coordinating the nutritional needs of a patient based on an affliction of the patient and, more particularly, to a method and system for developing and delivering a customized therapeutic meal plan program for a patient that is designed to ease the side effects of chemotherapy, introduce cancer inhibiting foods, and improve general nutrition for cancer patients.

Chemotherapy agents are commonly used as part of a treatment regiment for several types of cancers as well as non-cancer conditions, such as multiple sclerosis, rheumatoid arthritis, and organ transplant. Generally, chemotherapy involves the delivery of toxic agents into the body intravenously, orally, or in another fashion that are designed to damage and ultimately destroy targeted cells within the patient. For example, chemotherapy is commonly used in a cancer treatment regiment to destroy or slow the growth of a malignant tumor located in the patient's body. Chemotherapy agents are also used after an organ transplantation to suppress the immune system to prevent rejection of the transplanted organ. Depending on the type and the dosage of the chemotherapy toxins, commonly patients suffer nausea and vomiting, which for some patients can be severe and ultimately debilitating.

As a result of this widespread reaction to chemotherapy, some oncologists are increasingly encouraging their patients to limit intake of certain types of food and emphasizing the benefits of other types of foods. This generally consists of the oncologist recommending classes of foods that have generally been found to be effective in reducing the effects of chemotherapy. From this generalized information, which generally does not take into account other food-related issues of the patient, such as allergies and intolerances, or other medical conditions, such as diabetes, the patient must then develop a customized meal plan that the patient believes is consistent with the generalized recommendations provided by the oncologist.

Some oncologists refer patients to, or the patients discover on their own, various other resources that provide information relating to recommended diets for patients undergoing a chemotherapy regiment. These references are generally are limited to print materials, DVDs, web pages, and the like, and while these resources contain information that may be generally helpful to a chemotherapy patient, the patient, in order to develop a customized meal plan, must coordinate the information from the various sources with the specifics of his or her cancer diagnosis, chemotherapy, and other medical/dietary conditions, if any.

Thus, in general, there is a dearth of practical information for dietary planning available to chemotherapy patients, and furthermore, there is certainly no "one-stop shop" for meal planning and fulfillment. Instead, the patient is required to do a significant quantity of research related to his or her specific diagnosis, physical condition, side effects, etc. in order to develop an appropriate meal plan and then purchase the appropriate foods and prepare the meals accordingly. As a result, many patients, even those who understand the benefits of nutritional well-being during a physically taxing therapy, are unlikely to maximize those benefits.

It is also worth noting that patients who participate in their own treatment plan may have a better attitude about the outcome, and such positive psychological effects are known to have positive physiological manifestations. Patients who have been diagnosed with cancer often feel particularly unable to control the treatment process, since treatment is typically mandated by specific standards of medical care based on the type and degree of the disease. This loss of control can produce a negative psychological effect. However, patients who address their body's unique, dynamic, and often demanding nutritional needs during chemotherapy may be able to regain a sense of control, diminishing the negative effects of an inability to participate in their treatment. The positive effect of daily, active, and thoughtful participation in the treatment process through commitment to a program of nutrition therapy is not insubstantial.

A number of web-based diet related systems have been developed that allow a user to customize a meal plan to meet specific health related goals, such as weight loss. Some of these systems take into account food allergies and intolerances, as well as diet-restrictive medical conditions, such as diabetes. These systems in general are designed to guide user selection of various proprietary foodstuffs that have been developed to meet the user's nutritional needs as well as their dietary needs, e.g., weight loss. One exemplary system is the "NutriSystem Advanced Men's Diabetic Program" commercially available through NutriSystem, Inc.

The customization of these types of programs is generally limited to user gender, weight, and food allergies/intolerances. The programs developed by these systems do not consider medications taken by the user and moreover, do not identify those foodstuffs that may be beneficial in combating or mitigating the side effects of those medications, such as chemotherapy agents, in developing a customized meal plan.

SUMMARY OF THE INVENTION

The present invention is directed to a method and system that allows a patient or caregiver to interactively customize a therapeutic meal plan and that delivers the corresponding food items to the patient or caregiver. In one embodiment, the food items are pre-packaged in ready-to-cook or easy-to-prepare packages. The invention further allows the patient or caregiver to revise the meal plan as the dietary needs change across the span of treatment. However, an aspect of the invention is designed to be predictive of the patient's future dietary needs so that adjustments are kept to a minimum. In accordance with another aspect, patients undergoing chemotherapy are provided with research tools and specific information related to nutritional support, via an online database, customer call center, or other means, to provide the patient with additional information relating to the importance of nutrition during chemotherapy, and to provide support for the patient during the physically and emotionally draining process of chemotherapy.

It is therefore an object of the invention to provide an interactive tool that allows a patient or caregiver to customize a therapeutic meal plan that is tailored to the patient's cancer and chemotherapy treatment.

It is a further object of the invention to deliver foodstuffs for the meal plan in prepackaged ready-to-cook or easy-to-prepare packaging.

It is yet another object of the invention to allow the patient, caregiver, or physician to make changes to the patient's profile based on changes in the cancer, chemotherapy treatment, or other medical/health related condition of the patient, and to revise the meal plan accordingly.

It is a further object of the invention to automatically generate and display a list of foods and corresponding serving size on a computer screen and allow a user, such as a patient, to navigate through the list to select foods for a customized meal plan.

It is a further object of the invention to develop a customized meal plan for a cancer patient that takes into account the chemotherapy regimen of the patient as well as other medical/health related issues of the patient, such as food allergies or intolerances.

Other objects, features, and advantages of the invention will become apparent to those skilled in the art from the following detailed description and accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings, in which like reference numerals represent like parts throughout, and in which.

DETAILED DESCRIPTION

Figure 1:
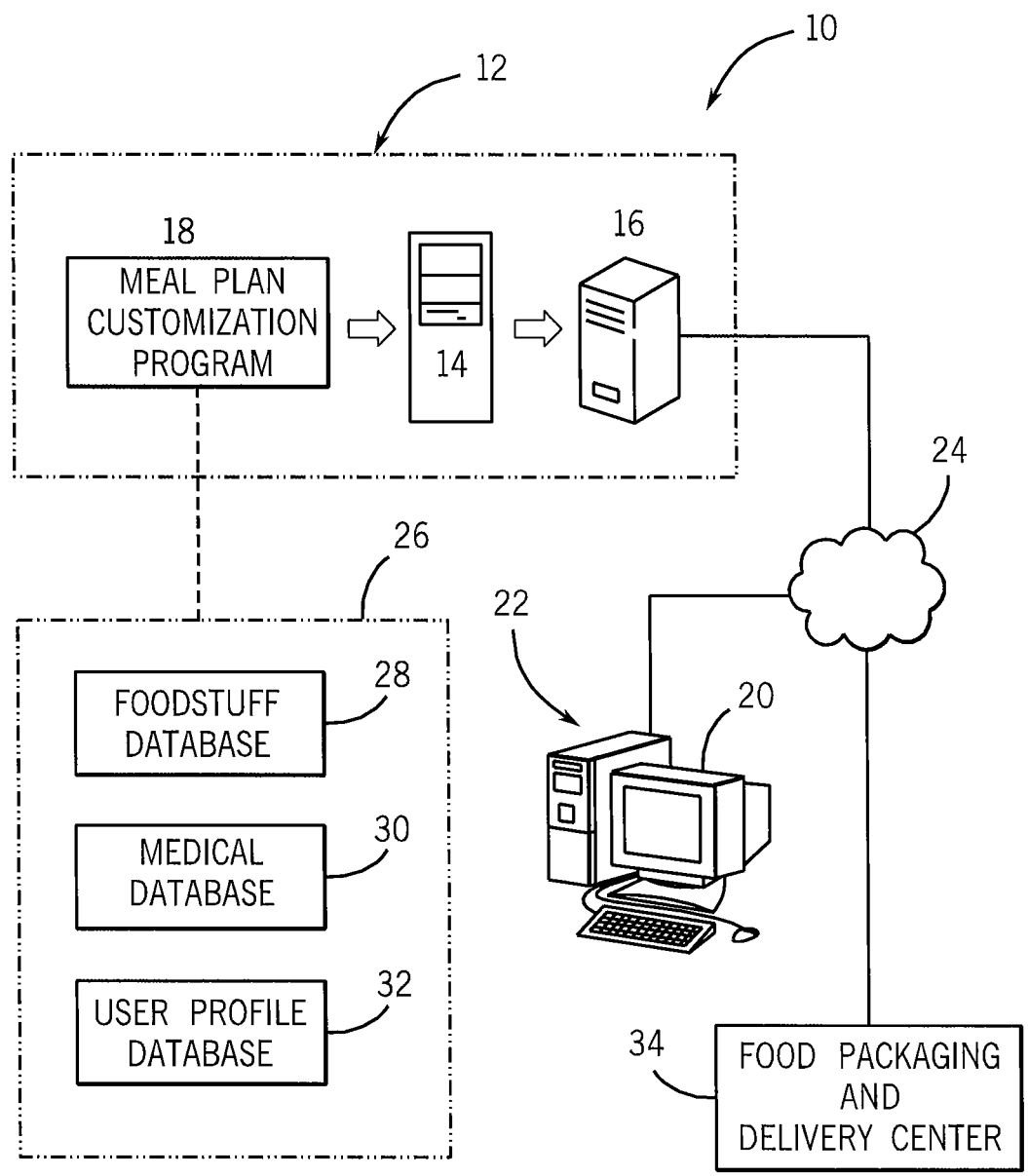
FIG. 1 is a schematic block diagram of a computerized system for developing a customized therapeutic meal plan for a cancer patient based on inputs received from a user.

Referring to FIG. 1, a computerized system 10 to facilitate customization of a meal plan designed to mitigate the effects of a chemotherapy treatment regiment in one embodiment is designed to be web-based and therefore includes a centralized facility 12 containing a computer 14 and a web server 16. The computer 14 is programmed to execute a meal plan customization program 18, which causes the web server 16 to display a series of windows (not shown) in a browser window (not shown) on a computer monitor 20 of a remote workstation 22. In a preferred embodiment, the remote workstation 22 communicates with the web server 16 via an internet connection 24, but is understood that other types of electronic communications could be used. The computerized system 10 also includes memory 26 containing a foodstuff database 28, a medical database 30, and a user profile database 32.

The foodstuff database 28 includes a list of foodstuffs available for inclusion in a customized meal plan. The list may include foodstuffs typically found at a grocery store which may be used to make one or more meals as well as pre-packaged proprietary meals. The medical database 30 contains information relating to the typical side effects of particular medicines as well as information regarding any dietary exclusions for particular medicines. For example, a patient taking Tamoxifen should not have flax seed or flax seed oil as part of his or her meal plan. The system 10 is designed to customize meal plans for multiple patients and, as such, the user profile database 32 may be used to store information for various users of the system, such as active or expired meal plans, health information, healthcare provider information, food allergies and intolerances, and contact information, for example.

In a preferred embodiment, the system 10 automates packaging and delivery of the food items of a customized meal plan directly to the patient. As such, a customized meal plan is transmitted to a food packaging and delivery center 34, that may be remote from the centralized facility 12, whereupon personnel at the center 34 assemble the food items contained in the customized meal plan, packages those items, and facilitates delivery of those items to the patient, or other designated individual, using a proprietary or common carrier.

The meal customization program 18 is designed to guide a user, such as a patient or the patient's caregiver or physician, through a meal customization process. The steps of that process are summarized in FIG. 2. As will be explained, the user is prompted to input patient physiological information and chemotherapy treatment information whereupon the program 18 identifies the daily nutritional needs of the patients and a list of food items that are believed to mitigate the effects of the chemotherapy treatment or otherwise improve the patient's readiness for the chemotherapy treatment.

The process 36 begins at block 38 whereupon the user is prompted to input data regarding the patient, such as age, gender, height, and weight at block 40. From this information, the program 18 identifies the patient's nutritional needs at block 42, such as daily caloric intake. The user is then prompted to identify the type of cancer and other related information for the patient at block 44. This may include the name as well as the stage of cancer, and those anatomical structures that are believed to contain cancerous cells. At block 46, the user is prompted to provide information regarding the chemotherapy treatment plan, such as type of chemotherapy agents, treatment schedule, and dosage. From this information, at block 48, the customization program accesses database 30 to determine what, if any, side effects may be experienced with the chemotherapy treatment plan and accesses database 38 to identify those foodstuffs that have been found to be effective in mitigating the identified side effects. The user is then prompted at block 50 to input any dietary restrictions or food allergies for the patient. The program 18 then integrates the identified food items that are believed to be successful in mitigating the anticipated side effects for the patient's chemotherapy treatment determined at block 48 and any dietary restrictions identified at block 50 to develop a list of recommend food items. The recommended list is then displayed at block 52 in a manner that allows a user to interactively select those food items the user wants included in the customized meal plan. This allows a user to customize the meal plan to account for any personal preferences of the patient. From the user selections provided at block 54 together with the nutritional needs information determined at block 42, a customized meal plan is developed at block 56.

It is contemplated that the meal plan may be presented as a list of ingredients and sample recipes using those ingredients that the patient or caregiver may purchase at the grocery store and prepare. Preferably, it is contemplated that the meal plan includes packaged meals that are delivered to the patient as ready-to-eat or ready-to-cook meals.

The program ends at block 58 with conveyance of the meal plan to the user or, if applicable, setting up payment and delivery of pre-packaged food items contained in the meal plan.

Figure 2:
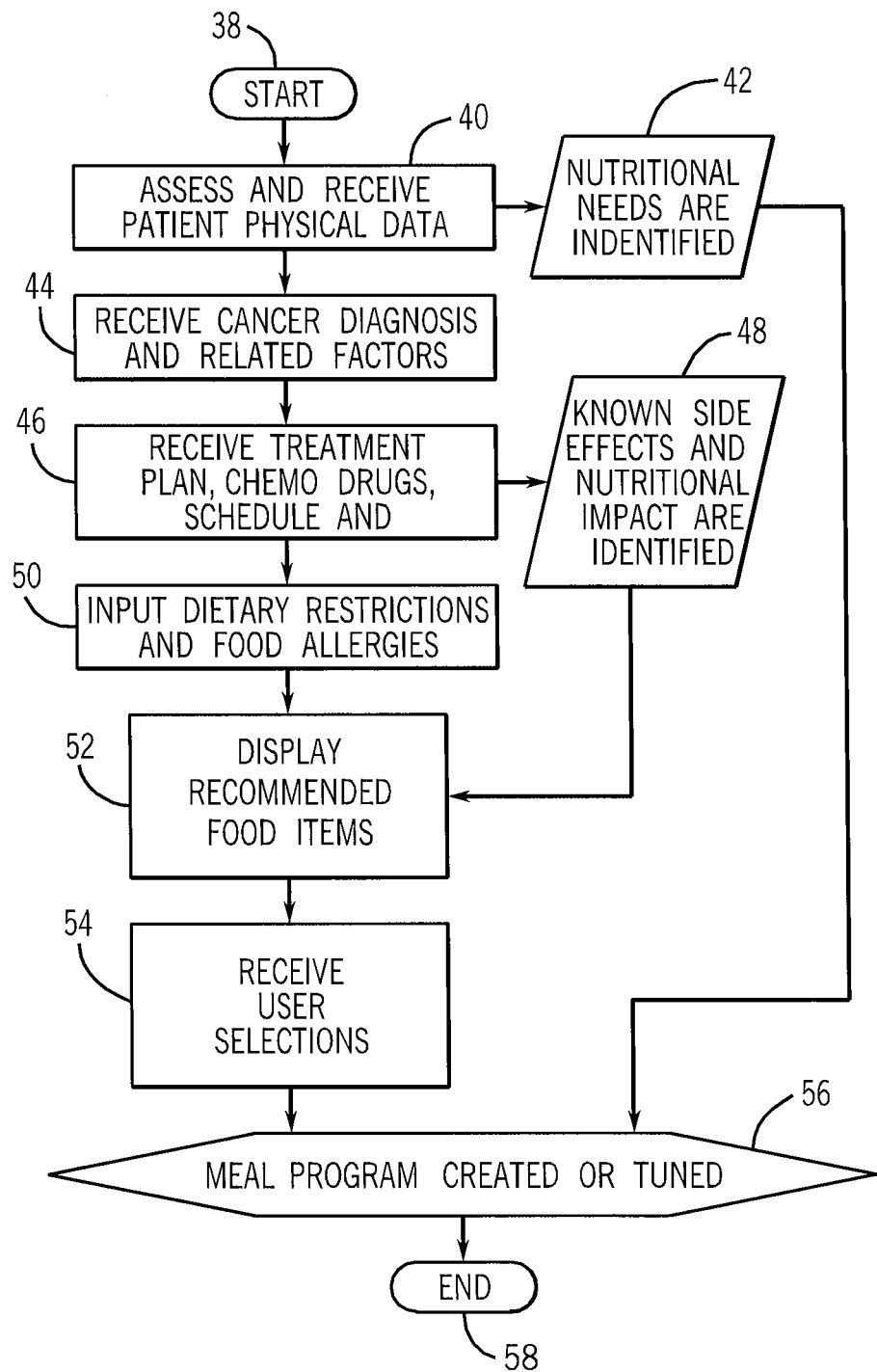
FIG. 2 is a flow chart setting forth the steps of developing a customized therapeutic meal plan for a cancer patient according to one embodiment of the present invention.
Figure 3:
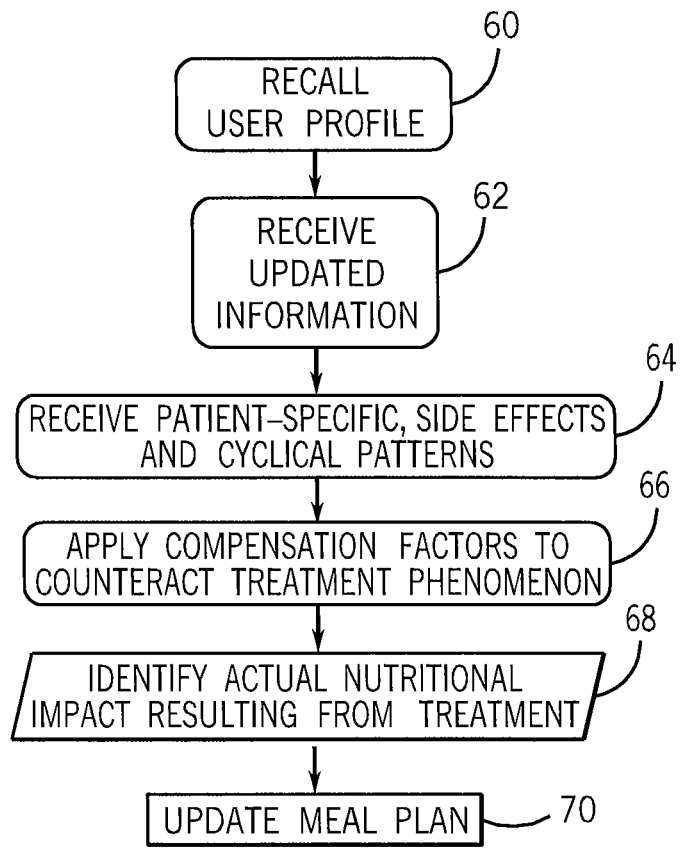
FIG. 3 is a flow chart setting forth the steps of updating a meal plan.

Referring now to FIG. 2, the present invention is designed to allow a user to dynamically customize a meal plan as changes in the patient's condition and/or treatment plan occur. In this regard, when appropriately instructed by a user input, the program recalls a patient profile at block 60 from the user profile database 32. The user is then prompted to provide updated information at block 62 regarding any changes in patient data, such as weight, changes in cancer information, such as stage, and changes in any food allergies or intolerances. Also, the initial meal plan is developed based on predicted side effects. The present invention also allows a user to identify specific side effects that have been experienced by the patient at block 64 so that the specifics of the patient's reaction to the chemotherapy treatment are considered in developing future meal plans. Similarly, the user can input information identifying the nutritional impact of the chemotherapy treatment at block 66. From this updated information, the program 18 applies compensation factors at block 68 to develop a revised meal plan at block 70.

While different patients' response to particular treatments varies, it has been found that an individual patient usually experiences the same side effects with each round of chemotherapy. Any major adjustment of the meal program created at block 56 therefore typically happens after the first round, and only fine tuning takes place in subsequent cycles.

In use and operation, after a patient receives his or her cancer diagnosis from a qualified physician, including type of cancer, stage of cancer, etc., an oncologist provides a treatment plan according to accepted standards of care. The treatment plan often includes one or more rounds of chemotherapy of variable intensity, radiation treatment, or a combination of the two, depending on the type and stage of cancer.

In a preferred embodiment, in preparation for and during chemotherapy, the patient uses a computer to access the program of the present invention. Alternately, the patient can call a participating registered dietitian or other program operator who uses a computer to access the program of the present invention. The program queries the patient for basic information such as height, weight, etc., as well as for health information that may impact a dietary plan, such as diabetes, food allergies, prescription medications that negatively interact with milk, antacids, etc. The program also prompts the patient to enter his or her specific diagnostic information and the date or dates for which chemotherapy has been scheduled. The program additionally requests patient food preferences such as, for example, "no fish" or "kosher" or "vegetarian."

It should be noted that the program can request information from the patient in any suitable order. For example, although many health care forms and institutions request routine information regarding pre-existing information such as a height and weight first, and information specific to a health condition such as type and degree of the health condition of concern last, it may be preferable to request the cancer specific information first in order to develop and maintain a patient's interest in the program.

After all required patient information is entered, the program compares the data input against a database containing dietary recommendations. The algorithm generates a recommended meal plan customized to the individual patient based on the input. For example, a patient taking Tamoxifen should not consume soy and most soy-based products; a patient who is preparing for a first round of chemotherapy may require additional antioxidant support in the form of a supplement or foods rich in antioxidants; a patient with esophageal cancer may require a bland, soft food diet; a patient with preexisting diabetes may have sugars restricted; a patient who is allergic to nuts will have products made on equipment that process nuts eliminated; etc.

The meal plan preferably incorporates a number of ready-to-eat meals, as well as a number of easy-to-prepare meals requiring the addition of a minimum of ingredients, and a minimum of time and effort to prepare. Fresh produce is also incorporated in the meal plan, as are "signature" or proprietary food items such as a day-of-chemo nutrition bar, an anti-nausea snack mix, teas formulated to combat specific side-effects, and others.

In a preferred embodiment, the program then requests a patient's meal plan choices. Specifically, the patient is provided with the option to purchase a full meal plan, a partial meal plan, and, if desired, add family portions of certain items to the meal plan. The meal plan may be selected for a number of days, a full week, or longer. Ideally, the patient preferably purchases a subscription for all or some portion of his or her chemotherapy treatment, since the advantages of dietary therapy are decreased when the plan is followed for only a short while or on a sporadic basis. Although it is hoped that patients will utilize dietary therapy throughout their chemotherapy regimen, preferably the patient orders frequently in order to report current side effects for which dietary therapy may be available. In a preferred embodiment, the patient orders at least once a week.

Access to the program may have other advantages, such as tools that provide and manage information relating to oncology and nutrition, specific side effects and treatments, nutritional recommendations, etc. These tools may be used merely as an education resource or may help a patient further fine tune his or her recommended nutrition plan.

The meal plan is then fulfilled in one or more stages by a service provider. In a first preferred stage, the service provider is at a first assembly location and receives the meal plan order after the patient's order has been placed online and payment has been verified. The foods called for in the patient's customized meal plan are supplied through a supply chain that may include contract food manufacturers, co-packers, food distributors, or other sources, and are delivered to the first assembly location. The supply chain may also include sources that deliver to a second assembly location or directly to the patient, such as one or more drop-ship distributors, retail outlets, or other suppliers.

The service provider preferably prepares, sorts and coordinates the foods called for in the patient's meal plan in a way that will increase the patient's ability to access, prepare, and eat the foods. For example, the foods could be arranged chronologically, e.g., Tuesday breakfast, Tuesday mid-morning snack, etc., or by category, e.g., all breakfast foods in one package, all interchangeable snacks in another, etc.

The service provider then ships the foods to the patient's home, or a location near the patient, or near the patient's cancer treatment center, or to another location convenient to the patient.

Because the meal plan comprises perishable foods, such as fruits, vegetables, fish, eggs, etc. and requires some mainstream ingredients found at any grocery store, such as safflower oil, peanuts, dried beans, etc., the service provider may supply the fresh foods and/or mainstream foods by first shipping the non-perishable prepackaged foods to a grocery store or other provider near the patient's pick-up location. The patient may then either purchase the fresh foods and/or mainstream ingredients at the time of pick-up, or a second assembly process, at the location nearer to the patient's pick-up location, can be employed to add the perishable foods and/or mainstream ingredients to the patient's order.

In another embodiment, the meal program queries the patient to determine whether necessary added ingredients such as oil are on hand. The program is preferably designed to offer the patient the option of adding the fresh foods and/or mainstream ingredients on his or her own, or of being supplied with those products by the service provider along with the pre-packaged food items, or of adding some fresh foods and/or mainstream ingredients on his or her own and being supplied with some fresh foods and/or mainstream ingredients based on preference, availability, seasonality, cost, or any other reason.

By way of example and not of limitation, a sample breast cancer case study is presented and a sample meal plan according to an embodiment of the program of the present invention is provided. Please note that the example assumes a typical treatment regimen but that a true treatment plan must be constructed in cooperation with an oncologist and oncology pharmacist. In no event should the materials set forth be construed as medical advice.

The tables set forth below contain sample data either provided by a user when prompted by the program or derived by the program using database information, as described above.

TABLE 1 patient physical data

| | |
|---|---|
| age | 55 years |
| sex | female |
| height | 5' 5" |
| current body weight | 145# (65.9 kg) |
| usual weight | 140# (63.6 kg) - 3 months ago |
| percent weight change | +3.5% × 3 months |
| ideal body weight (IBW) | 125# (56.8 kg) |
| body mass index (BMI) | 24.12 |
| current activity level | sedentary |
| current medications | none |
| past medical history (nutritional) | none |
| nutritional supplements | multivitamin |
| herbal supplements | none |

TABLE 2 patient dietary data

| | |
|---|---|
| dietary restrictions | vegetarian |
| food allergies | none |
| nutrition-related symptoms | none at this time |

TABLE 3 patient diagnosis data

| | |
|---|---|
| diagnosis | Invasive Ductal Carcinoma |
| hormone status | Estrogen Receptor Positive (ER+) |
| | Progesterone Receptor Negative (PR−) |
| | HER2-neg |
| tumor grade | T2N0M0 (Stage IIA) |

TABLE 4 patient treatment plan

| | |
|---|---|
| lumpectomy | yes |
| | date = [1 week] |
| radiation therapy | yes |
| | daily |
| | start date = [3 weeks] |
| | end date = [start date + 6 weeks] |
| adjuvant chemotherapy | yes |
| | concurrent with radiation therapy: CMF |
| | (cyclophosphamide, methotrexate, fluorouracil) |
| Tamoxifen | yes |
| | concurrent with radiation and chemotherapy |
| | continue for 5 years. |

TABLE 5

| action | recommendation |
|---|---|
| nutritional needs | 1650 calories (25 kcals/kg current body weight) |
| | 57-85 g protein (1.0-1.5 g protein/kg IBW) |
| nutritional needs | I lumpectomy |
| |   i no dietary therapy known |
| | II radiation therapy |
| |   i no dietary therapy known |
| | III chemotherapy |
| |   i Cyclophosphamide |
| |     (a) anorexia |
| |       1. may require calorie/protein dense foods |
| |       2. wait for symptoms to start |
| |     (b) weight loss |
| |       1. may require calorie/protein dense foods |
| |       2. wait for symptoms to start |
| |     (c) fatigue |
| |       1. ready to serve meals |
| |       2. protein dense foods |
| |       3. wait for symptoms to start |
| |   ii Methotrexate |
| |     (a) nausea |
| |       1. bland, starchy foods |
| |       2. small, frequent meals |
| |       3. wait for symptoms to start |
| |     (b) vomiting |
| |       1. diet as tolerated |
| |       2. wait for symptoms to start |
| |     (c) anorexia |
| |       1. may require calorie/protein dense foods |
| |       2. wait for symptoms to start |
| |     (d) mucositis |
| |       1. bland, soft foods |
| |       2. wait for symptoms to start |
| |     (e) esophagitis |
| |       1. bland, soft foods |
| |       2. wait for symptoms to start |
| |     (f) diarrhea |
| |       1. starchy foods |
| |       2. low fiber (BRAT) diet |
| |       3. wait for symptoms to start |
| |     (g) taste changes |
| |       1. diet as tolerated |
| |       2. wait for symptoms to start |
| |   iii Fluorouracil |
| |     (a) anorexia |
| |       1. may require calorie/protein dense foods |
| |       2. wait for symptoms to start |
| |     (b) hand and feet neuropathy |
| |       1. glutamine supplementation, 10 grams, three times daily |
| |       2. recommend prophylactic treatment |
| |     (c) mucositis, esophagitis |
| |       1. glutamine supplementation, 10 grams, three times daily |
| |       2. swish and swallow |
| |       3. recommend prophylactic treatment |
| |     (d) diarrhea |
| |       1. BRAT diet |
| |       2. glutamine supplementation, 10 grams, three times daily |
| |       3. recommend prophylactic treatment |
| |   iv Tamoxifen |
| |     (a) nausea |
| |       1. bland, starchy foods |
| |       2. small, frequent meals |
| |       3. wait for symptoms to start |
| oncology dietetic recommendations | I glutamine |
| |   i recommend prophylactic glutamine supplementation |
| |   ii 10 g three times daily while on fluorouracil treatment |
| | II Tamoxifen |

TABLE 5-continued

| action | recommendation |
|---|---|
| | i no flax seed or flax seed oil |
| | ii no soy foods or soy supplements including tofu, soy milk, soy nuts, tempeh, miso, soy protein, soy protein isolate, soy flour |
| | iii allowed: soy sauce, soy lecithin, soybean oil |
| | III recommended food group servings based on 1600 calorie diet. |
| | i Grains: 5 oz |
| | ii Vegetables: 2 cups |
| | iii Dairy: 3 cups |
| | iv Protein: 5 oz |
| | v Fats: 5 tsp oil |
| | IV calcium and vitamin D |
| | i bone loss and decreased bone strength are significant long-term complications of chemotherapy |
| | ii adequate intake of calcium and vitamin D is essential |
| | iii recommended dietary intake for women age 30 and older is 1,000-1,200 mg calcium and 200-600 IU of vitamin D (Food and Nutrition Information Center; 2004) |
| | iv many oncology dietitians feel that the RDI for vitamin D is set too low |
| | v 1000-1500 IU/day is a common recommendation in practice |
| | vi 2000 IU/day is the upper limit from all food and supplemental sources |
| | V alcohol |
| | i recommend less than 1 drink/day |
| | VI weight |
| | i maintenance is main nutritional goal |
| | ii weight loss not advised during treatment |
| | iii weight gain is a concern |
| | (a) "Between 50%-96% of women who have adjuvant chemotherapy will gain weight, and many will maintain this potentially dangerous new weight". |
| | (b) weight gain may increase risk for recurrence |
| | iv weight loss is acceptable after treatment is completed |
| meal program generated | see meal plan at table 6 below |
| | see supplement plan at table 7 below |
| | see beverage options at table 8 below |
| | 1600 calorie diet |
| | vegetarian menu options (omitting flax and soy items) |
| | offer "day of chemo" menu during adjuvant chemotherapy cycles |

TABLE 6

| day | breakfast | am snack | lunch | pm snack | dinner | evening snack/dessert |
|---|---|---|---|---|---|---|
| 1 | enriched flake cereal, skim milk, berries | yogurt & fruit smoothie with whey protein | ALT (avocado, lettuce, tomato sandwich), side salad | whole grain crackers w/ veggie spread | mushroom barley soup, large garden salad | dark chocolate dipped strawberries |
| 2 | baked French toast, skim milk, fruit | hard boiled egg, fruit | tuna salad on whole grain bread, baby carrots, cowboy bean salad | yogurt & fruit smoothie with whey protein | veggie wrap, spicy Mexican beans, vegetable chips | hot fruit compote |
| 3 (c) | proprietary breakfast bar, skim milk, fruit | yogurt & fruit smoothie with whey protein | peanut butter & jelly sandwich, berries, pretzels with mustard dip | roasted nut meal, whole wheat crackers | vegetable soup, whole grain crackers | gingerbread cookies w/ tea |
| 4 | apple bran muffin, hard boiled egg, skim milk, fruit | rice cakes with fruit spread | vegetable chili, side salad | yogurt & fruit smoothie with whey protein | curried shrimp w/ basmati rice & peas, applesauce | lemon pound cake w/ raspberries |
| 5 | apple cinnamon oatmeal, skim milk, fruit | yogurt & fruit smoothie with whey protein | fruity couscous salad, raw broccoli & cauliflower | hummus & veggies | pumpkin soup, large garden salad | pear crisp |
| 6 | pumpkin & bran pancakes, skim milk, fruit | bean dip w/ vegetable chips | Moroccan stew, green vegetables with yogurt dip | yogurt & fruit smoothie with whey protein | tomato & garlic bread gnocchi, steamed broccoli & cauliflower | dark chocolate pudding |
| 7 | proprietary breakfast bar, skim milk, fruit | yogurt & fruit smoothie with whey protein | black bean salad, whole grain crackers with cheese | brazil nuts, almonds and sunflower seeds | salmon cakes, Swiss chard, brown rice pilaf | dark chocolate dipped strawberries |
| 8 | blueberry muffin, scrambled eggs, fruit, skim milk | proprietary dried fruit & nut mix | sun dried spinach & tomato tortellini, side salad | yogurt & fruit smoothie with whey protein | spinach & ginger stir fry, brown rice, applesauce | hot fruit compote |

TABLE 6-continued

| day | breakfast | am snack | lunch | pm snack | dinner | evening snack/ dessert |
|---|---|---|---|---|---|---|
| 9 | enriched flake cereal, skim milk, berries | yogurt & fruit smoothie with whey protein | pinto bean soup, side salad | whole grain crackers w/ veggie spread | lemon baked cod w/ limonene, curried cauliflower, sweet potato w/ ginger | ginger banana |
| 10 | apple cinnamon oatmeal, skim milk, fruit | guacamole with vegetable chips | veggie wrap, cole slaw | yogurt & fruit smoothie with whey protein | mushroom & leek manicotti, braised leeks | dark chocolate dipped strawberries |
| 11 | proprietary breakfast bar, skim milk, fruit | yogurt & fruit smoothie with whey protein | barley stew, zucchini bran bread | bean dip w/ vegetable chips | garlic sesame salad, blueberry muffin | sweet potato pudding |
| 12 | baked French toast, skim milk, fruit | hummus & veggies | gazpacho soup, whole grain crackers with cheese | yogurt & fruit smoothie with whey protein | sweet potato soup, large garden salad | baked cinnamon apple |
| 13 | low fat yogurt, oats, fruit, pomegranate juice | yogurt & fruit smoothie with whey protein | yam veggie wrap, bean dip with vegetable chips | guacamole with vegetable chips | tuna cakes, curried carrots, quinoa | pear crisp |
| 14 | blueberry muffin, scrambled eggs, fruit, skim milk | rice cakes with fruit spread | spinach & tomato salad, whole grain crackers with cheese | yogurt & fruit smoothie with whey protein | winter squash soup, large garden salad | chewy carrot brownies |

(c) represents day of chemo menu

TABLE 7 daily supplementation 10 g glutamine mixed in applesauce or juice three times/day
proprietary multivitamin
1000 IU vitamin D supplement
Florajen3 Probiotic
1 scoop whey protein
1 g fish oil

TABLE 8 beverage options skim milk
rice milk
proprietary tea
cranberry juice
pomegranate juice
proprietary vegetable juice
Boost ®/Ensure ®
proprietary lemonade
proprietary bottled water
fruit smoothies
ginger ale
watermelon slush
cantaloupe banana smoothie
green tea slush with apricot nectar
whole milk
proprietary hot cocoa mix The embodiment described herein explains the best known mode of practicing the invention and will enable others skilled in the art to utilize the invention, but should not be considered limiting. Rather, it should be understood that the invention is not limited to the details and arrangements set forth herein, but is capable of other embodiments and of being practiced or carried out in various ways, and all such modifications and variations are within the scope of the present invention. For example, while the preferred embodiment calls for a patient's use of a computer having internet access to enter data and order foods from the meal plan, the patient may telephone a nutritional counselor who requests the patient's information, enters the data into the computer program, and orders foods for delivery to the patient location.

Various elements or features discussed herein may also be combined in ways other than those specifically mentioned, and all such combinations are likewise within the scope of the invention. For example, while it is believed that maximum results are achieved by a full meal plan for the duration of his or her treatment course, the patient may instead choose to purchase for only one week, such as the week of chemotherapy, or the patient may choose to purchase "signature" food items a la carte, such as the day-of-chemo nutrition bar, or teas specially formulated to combat particular side effects, without purchase of a meal program.

Many other changes and modifications could be made to the invention without departing from the spirit thereof, and the scope of these changes will be apparent from the appended claims.

We claim:

1. A method for customizing a therapeutic meal plan for a patient comprising the steps of:
   providing an interactive user interface to a user;
   receiving a first input to the interactive user interface from the user containing cancer identifying information relating to a cancer that has stricken a patient;
   receiving a second input to the interactive user interface from the user containing chemotherapy information related to a chemotherapy treatment for the patient including at least one of type of chemotherapy agents, treatment schedule, and dosage;

allowing at least one of patient, caregiver, and physician to make changes to a patient profile based on changes in at least one of a health condition and the chemotherapy treatment for the patient associated with the health condition;

determining and displaying a list of recommended food items for the patient on the user interface based on the first input and the second input including the chemotherapy information related to the chemotherapy treatment for the patient including at least one of type of chemotherapy agents, treatment schedule, and dosage;

prompting the user to select one or more food items from the list of recommended food items;

developing and conveying a meal plan to the user via the user interface based on a user selection of the one or more food items;

assembling the selected food items; and delivering the selected food items to the user.

2. The method of claim 1, wherein developing the meal plan includes determining a recommended caloric need for the patient and automatically determining serving sizes for the selected food items based on the recommended caloric need.

3. The method of claim 1, further comprising receiving a third input identifying a change in the first input or the second input, and further comprising automatically revising the list of recommended foods based on the third input.

4. The method of claim 1, wherein the meal plan excludes any food items to which the patient is allergic or of which the patient is intolerant.

5. The method of claim 1, further comprising receiving a third input to the user interface from the user containing information regarding non-cancer related health issues of the patient and considering the non-cancer related health issues in developing the list of recommended food items.

6. The method of claim 1, wherein the selected food items comprise ready-to-eat food items.

7. The method of claim 1, wherein the selected food items are contained in ready-to-cook packages.

8. A computer implemented method for customizing a therapeutic meal plan for a patient comprising the steps of:

providing an interactive user interface to a user;

receiving a first input to the interactive user interface from the user containing cancer identifying information relating to a cancer that has stricken the patient;

receiving a second input to the interactive user interface from the user containing chemotherapy information related to a chemotherapy treatment for the patient including type of chemotherapy agents, treatment schedule, and dosage;

determining any side effects relating the chemotherapy treatment;

determining and displaying, by the computer, a list of recommended food items for the patient on the user interface based on the first input and the second input and any side effects relating to the chemotherapy treatment to mitigate the side effects and anticipated side effects relating to the chemotherapy treatment and dietary restrictions associated with the patient;

prompting the user to select one or more of the food items from the list of recommended food items; and developing and transmitting the therapeutic meal plan to the user via the user interface based on a user selection of the one or more food items.

9. The method of claim 8, wherein said receiving the second input further comprises receiving the second input from the user comprising information related to a treatment for the patient associated with the health condition including medications taken by the user, and wherein said determining further comprises determining and displaying the list of recommended food items that may be beneficial in combating or mitigating the side effects of the medications in developing the therapeutic meal plan customized for the user.

10. The method of claim 9, wherein the user comprises at least one of a patient, caregiver, and physician, and wherein the developing and conveying the therapeutic meal plan further comprises allowing the at least one of patient, caregiver, and physician to make changes to a patient profile based on changes in at least one of the health condition and the treatment for the patient associated with the health condition.

11. The method of claim 10, wherein said method further comprises storing a plurality of user profiles corresponding to a plurality of users, each of the profiles including, when present, active or expired meal plans, health information, healthcare provider information, food allergies and intolerances, and contact information, and wherein said determining further comprises determining and displaying a list of recommended food items for the patient on the user interface based on the first input comprising the identifying information relating to the health condition, the second input comprising the information related to the treatment for the patient and the user information stored in a user profile in developing the therapeutic meal plan customized for the user.

12. The method of claim 1, wherein the step of receiving the second input further comprises receiving the second input to the interactive user interface from the user containing particular chemotherapy information related to a chemotherapy treatment regimen developed to treat the medical condition of the patient, and wherein the determining and displaying the list of recommended food items for the patient further comprises determining and displaying the list of recommended food items for the patient on the user interface based on the first input and the second input including the chemotherapy information related to the chemotherapy treatment regimen developed to treat the medical condition of the patient.

13. The method of claim 1, further comprising receiving a third input identifying information regarding specific side effects that have actually been experienced by the patient in reaction to the patient's specific chemotherapy treatment, and wherein the determining and displaying further comprises determining and displaying the list of recommended food items for the patient on the user interface responsive to the first, second and third inputs.

14. The method of claim 1, further comprising identifying predicted side effects of the patient's specific chemotherapy treatment, and their nutritional impact, and the determining and displaying further comprises determining and displaying the list of recommended food items for the patient on the user interface responsive to the identifying the predicted side effects of the patient's specific chemotherapy treatment.

15. The method of claim 14, further comprising receiving a third input identifying information regarding specific side effects that have actually been experienced by the patient in reaction to the patient's specific chemotherapy treatment, and wherein the determining and displaying further comprises determining and displaying the list of recommended food items for the patient on the user interface responsive to the first, second and third inputs.

16. The method of claim 1, further comprising enabling the at least one of patient, caregiver, and physician to make changes to a patient profile based on changes in health condition and at least one of current and future treatment for the patient associated with the health condition.

17. The method of claim 1, further comprising:
enabling the at least one of patient, caregiver, and physician to make changes to a patient profile based on changes in health condition and at least one of current and future treatment for the patient associated with the health condition, including changes in weight, cancer information including stage of cancer, food allergies and food intolerances;
updating the patient profile responsive to the changes in the patient profile; and
developing and conveying the meal plan to the user via the user interface based on the user selection and the updated patient profile.

18. The method of claim 17, further comprising:
enabling the at least one of patient, caregiver, and physician to make additional changes to a patient profile based on at least one of actual and predicted side effects to the chemotherapy treatment;
updating the patient profile responsive to the changes and the additional changes in the patient profile; and
developing and conveying the meal plan to the user via the user interface based on the user selection and the updated patient profile.

19. The method of claim 18, further comprising:
enabling the at least one of patient, caregiver, and physician to make additional changes to a patient profile based the nutritional impact of the chemotherapy treatment;
updating the patient profile responsive to the changes and the additional changes in the patient profile; and
developing and conveying the meal plan to the user via the user interface based on the user selection, at least one compensation factor and the updated patient profile.

20. The method of claim 10, further comprising enabling the at least one of patient, caregiver, and physician to make changes to a patient profile based on changes in health condition and at least one of current and future treatment for the patient associated with the health condition.

21. A method for customizing a therapeutic meal plan for a patient comprising the at least one of sequential, non-sequential and sequence independent steps of:
providing an interactive user interface to a user;
receiving a first input to the interactive user interface from the user containing cancer identifying information relating to a cancer that has stricken the patient;
receiving a second input to the interactive user interface from the user containing chemotherapy information related to a chemotherapy treatment for the patient including at least one of type of chemotherapy agents, treatment schedule, and dosage;
receiving, when available, a third input identifying information regarding specific side effects that have actually been experienced by the patient in reaction to the patient's specific chemotherapy treatment;
allowing the at least one of patient, caregiver, and physician to make changes to a patient profile based on changes in at least one of the health condition, the treatment for the patient associated with the health condition and the specific side effects actually experienced by the patient in reaction to the patient's specific chemotherapy treatment;
determining and displaying a list of recommended food items for the patient on the user interface based on the first input, the second input including the chemotherapy information related to the chemotherapy treatment for the patient including at least one of type of chemotherapy agents, treatment schedule, and dosage and, when available, the third input;
prompting the user to select one or more of food items from the list of recommended food items;
developing and conveying the meal plan to the user via the user interface based on a user selection of the one or more food items;
assembling the selected food items; and
delivering the selected food items to the user.

22. The method of claim 21, wherein developing the meal plan includes determining a recommended caloric need for the patient and automatically determining serving sizes for the selected food items based on the recommended caloric need.

23. The method of claim 21, further comprising at least one of receiving a fourth input identifying a change in the first input or the second input, and receiving the third input subsequent to the determining and displaying the list of recommended food items, and further comprising automatically revising the list of recommended food items based on at least one of the fourth input and the subsequently received third input.

24. The method of claim 21, wherein the meal plan excludes any food items to which the patient is allergic or of which the patient is intolerant.

25. The method of claim 21, further comprising receiving a fourth input to the user interface from the user containing information regarding non-cancer related health issues of the patient and considering the non-cancer related health issues in developing the recommended list of food items.

26. The method of claim 21, wherein the selected food items comprise ready-to-eat food items.

27. The method of claim 21, wherein the selected food items are contained in ready-to-cook packages.

28. The method of claim 21, wherein the step of receiving the second input further comprises receiving the second input to the interactive user interface from the user containing particular chemotherapy information related to a chemotherapy treatment regimen developed to treat the medical condition of the patient, and wherein the determining and displaying the list of recommended food items for the patient further comprises determining and displaying the list of recommended food items for the patient on the user interface based on the first input, the second input including the chemotherapy information related to the chemotherapy treatment regimen developed to treat the medical condition of the patient, and, where available, the third input.

29. The method of claim 21, wherein the determining and displaying further comprises determining and displaying the list of recommended food items for the patient on the user interface responsive to the first input, the second input and, when available, the third input.

30. The method of claim 21, further comprising identifying predicted side effects of the patient's specific chemotherapy treatment, and their nutritional impact, and the determining and displaying further comprises determining and displaying the list of recommended food items for the patient on the user interface responsive to the identifying the predicted side effects of the patient's specific chemotherapy treatment.

31. The method of claim 30, wherein the determining and displaying further comprises determining and displaying the list of recommended food items for the patient on the user interface responsive to the first, second, and, when available, third inputs.

32. The method of claim 21, further comprising enabling the at least one of patient, caregiver, and physician to make changes to a patient profile based on changes in health condition and at least one of current and future treatment for the patient associated with the health condition.

33. The method of claim 21, further comprising:
enabling the at least one of patient, caregiver, and physician to make changes to a patient profile based on changes in health condition and at least one of current and future treatment for the patient associated with the health condition, including changes in weight, cancer information including stage of cancer, food allergies and food intolerances;
updating the patient profile responsive to the changes in the patient profile; and
developing and conveying the meal plan to the user via the user interface based on the user selection and the updated patient profile.

34. The method of claim 33, further comprising:
enabling the at least one of patient, caregiver, and physician to make additional changes to the patient profile based on at least one of actual and predicted side effects to the chemotherapy treatment;
updating the patient profile responsive to the changes and the additional changes in the patient profile; and
developing and conveying the meal plan to the user via the user interface based on the user selection and the updated patient profile.

35. The method of claim 34, further comprising:
enabling the at least one of patient, caregiver, and physician to make additional changes to a patient profile based the nutritional impact of the chemotherapy treatment;
updating the patient profile responsive to the changes and the additional changes in the patient profile; and
developing and conveying the meal plan to the user via the user interface based on the user selection, at least one compensation factor and the updated patient profile.

* * * * *